United States Patent
Lakin et al.

(10) Patent No.: US 7,780,676 B2
(45) Date of Patent: Aug. 24, 2010

(54) INTERVERTEBRAL IMPLANTATION APPARATUS

(75) Inventors: Ryan Cameron Lakin, Newton, NJ (US); Kirk J. Bailey, Blairstown, NJ (US); John M. Blumers, Mendham, NJ (US)

(73) Assignee: EBI, LLC, Parsippany, NJ (US)

( * ) Notice: Subject to any disclaimer, the term of this patent is extended or adjusted under 35 U.S.C. 154(b) by 425 days.

(21) Appl. No.: 11/775,303

(22) Filed: Jul. 10, 2007

(65) Prior Publication Data

US 2008/0015702 A1   Jan. 17, 2008

Related U.S. Application Data

(60) Provisional application No. 60/830,153, filed on Jul. 11, 2006.

(51) Int. Cl.
*A61B 17/58* (2006.01)
*A61B 17/60* (2006.01)
*A61F 2/00* (2006.01)

(52) U.S. Cl. ............ 606/99; 606/279; 623/17.16

(58) Field of Classification Search ... 623/17.11–17.16; 606/99, 86 A, 100, 246–249, 279
See application file for complete search history.

(56) References Cited

U.S. PATENT DOCUMENTS

| | | | |
|---|---|---|---|
| 3,848,601 A | 11/1974 | Ma et al. |
| 3,875,595 A | 4/1975 | Froning |
| 3,892,232 A | 7/1975 | Neufeld |
| 4,272,855 A | 6/1981 | Frey et al. |
| 4,309,777 A | 1/1982 | Patil |
| 4,341,206 A | 7/1982 | Perrett et al. |
| 4,349,921 A | 9/1982 | Kuntz et al. |
| 4,450,834 A | 5/1984 | Fischer |
| 4,501,269 A | 2/1985 | Bagby |
| 4,526,909 A | 7/1985 | Urist |
| 4,596,574 A | 6/1986 | Urist |
| 4,599,086 A | 7/1986 | Doty |
| 4,620,327 A | 11/1986 | Caplan et al. |
| 4,623,553 A | 11/1986 | Ries et al. |
| 4,714,469 A | 12/1987 | Kenna |
| 4,743,256 A | 5/1988 | Brantigan |
| 4,759,766 A | 7/1988 | Buettner-Janz et al. |
| 4,772,287 A | 9/1988 | Ray et al. |
| 4,878,915 A | 11/1989 | Brantigan |
| 4,997,432 A | 3/1991 | Keller et al. |
| 5,015,247 A | 5/1991 | Michelson |
| 5,026,373 A | 6/1991 | Ray et al. |

(Continued)

FOREIGN PATENT DOCUMENTS

DE   2263842   7/1974

(Continued)

*Primary Examiner*—Eduardo C Robert
*Assistant Examiner*—Christina Negrelli
(74) *Attorney, Agent, or Firm*—Harness, Dickey

(57) ABSTRACT

An implantation apparatus for preparing adjacent vertebral bodies to receive an intervertebral implant including a plurality of keels. The implantation apparatus includes an elongated handle portion, and a template portion carried at a distal end of the handle portion substantially perpendicularly to the handle portion. The template portion defines a plurality of open channels corresponding in position and shape of the plurality of keels. Each channel is positioned and shaped for preparing a vertebral opening to receive a corresponding keel.

13 Claims, 5 Drawing Sheets

U.S. PATENT DOCUMENTS

| | | |
|---|---|---|
| 5,147,402 A | 9/1992 | Bohler et al. |
| 5,258,031 A | 11/1993 | Salib et al. |
| 5,258,043 A | 11/1993 | Stone |
| 5,282,861 A | 2/1994 | Kaplan |
| 5,306,307 A | 4/1994 | Senter et al. |
| 5,306,308 A | 4/1994 | Gross et al. |
| 5,306,309 A | 4/1994 | Wagner et al. |
| 5,308,412 A | 5/1994 | Shetty et al. |
| 5,314,477 A | 5/1994 | Marnay et al. |
| 5,397,364 A | 3/1995 | Kozak et al. |
| 5,401,269 A | 3/1995 | Buttner-Janz et al. |
| 5,415,704 A | 5/1995 | Davidson |
| 5,425,772 A | 6/1995 | Brantigan |
| 5,425,773 A | 6/1995 | Boyd et al. |
| 5,443,515 A | 8/1995 | Cohen et al. |
| 5,484,437 A | 1/1996 | Michelson |
| 5,505,732 A | 4/1996 | Michelson |
| 5,507,816 A | 4/1996 | Bullivant et al. |
| 5,514,180 A | 5/1996 | Heggeness et al. |
| 5,522,899 A | 6/1996 | Michelson |
| 5,534,029 A | 7/1996 | Shima et al. |
| 5,534,030 A | 7/1996 | Navarro et al. |
| 5,556,431 A | 9/1996 | Buttner-Janz et al. |
| 5,573,537 A | 11/1996 | Rogozinski |
| 5,593,409 A | 1/1997 | Michelson |
| 5,609,635 A | 3/1997 | Michelson |
| 5,645,596 A | 7/1997 | Kim et al. |
| 5,658,336 A | 8/1997 | Pisharodi |
| 5,674,294 A | 10/1997 | Bainville et al. |
| 5,674,296 A | 10/1997 | Bryan et al. |
| 5,676,701 A | 10/1997 | Yuan et al. |
| 5,720,748 A | 2/1998 | Kuslich et al. |
| 5,741,253 A | 4/1998 | Michelson |
| 5,772,661 A | 6/1998 | Michelson |
| 5,782,832 A | 7/1998 | Larsen et al. |
| 5,785,710 A | 7/1998 | Michelson |
| 5,797,909 A | 8/1998 | Michelson |
| 5,860,973 A | 1/1999 | Michelson |
| 5,888,222 A | 3/1999 | Coates et al. |
| 5,888,226 A | 3/1999 | Rogozinski |
| 5,899,908 A | 5/1999 | Kuslich et al. |
| 5,899,941 A | 5/1999 | Nishijima et al. |
| 5,947,971 A | 9/1999 | Kuslich et al. |
| 6,004,326 A | 12/1999 | Castro et al. |
| 6,019,792 A | 2/2000 | Cauthen |
| 6,039,763 A | 3/2000 | Shelokov |
| 6,080,155 A | 6/2000 | Michelson |
| 6,096,038 A | 8/2000 | Michelson |
| 6,113,637 A | 9/2000 | Gill et al. |
| 6,120,502 A | 9/2000 | Michelson |
| 6,123,705 A | 9/2000 | Michelson |
| 6,149,650 A | 11/2000 | Michelson |
| 6,171,339 B1 | 1/2001 | Houfburg et al. |
| 6,224,595 B1 | 5/2001 | Michelson |
| 6,264,656 B1 | 7/2001 | Michelson |
| 6,270,498 B1 | 8/2001 | Michelson |
| 6,283,966 B1 | 9/2001 | Houfburg |
| 6,332,887 B1 | 12/2001 | Knox |
| 6,368,350 B1 | 4/2002 | Erickson et al. |
| 6,402,785 B1 | 6/2002 | Zdeblick et al. |
| 6,413,278 B1 | 7/2002 | Marchosky |
| 6,416,551 B1 | 7/2002 | Keller |
| 6,423,095 B1 | 7/2002 | Van Hoeck et al. |
| 6,440,139 B2 | 8/2002 | Michelson |
| 6,440,168 B1 | 8/2002 | Cauthen |
| 6,517,580 B1 | 2/2003 | Ramadan et al. |
| 6,540,753 B2 | 4/2003 | Cohen |
| 6,540,785 B1 | 4/2003 | Gill et al. |
| 6,582,432 B1 | 6/2003 | Michelson |
| 6,749,635 B1 | 6/2004 | Bryan |
| 6,881,228 B2 | 4/2005 | Zdeblick et al. |
| 6,896,676 B2 | 5/2005 | Zubok et al. |
| 6,994,728 B2 | 2/2006 | Zubok et al. |
| 6,997,954 B2 | 2/2006 | Zubok et al. |
| 7,025,787 B2 | 4/2006 | Bryan et al. |
| 7,048,764 B2 | 5/2006 | Ferree |
| 7,083,623 B2 | 8/2006 | Michelson |
| 7,115,128 B2 | 10/2006 | Michelson |
| 2002/0035400 A1 | 3/2002 | Bryan et al. |
| 2002/0143343 A1 | 10/2002 | Castro |
| 2002/0198533 A1 | 12/2002 | Geisler et al. |
| 2003/0009224 A1 | 1/2003 | Kuras |
| 2003/0065394 A1 | 4/2003 | Michelson |
| 2003/0100951 A1 | 5/2003 | Serhan et al. |
| 2003/0139816 A1 | 7/2003 | Michelson |
| 2003/0199982 A1 | 10/2003 | Bryan |
| 2004/0002758 A1 | 1/2004 | Landry et al. |
| 2004/0117022 A1 | 6/2004 | Marnay et al. |
| 2004/0143270 A1 | 7/2004 | Zucherman et al. |
| 2004/0176774 A1 | 9/2004 | Zubok et al. |
| 2004/0176777 A1 | 9/2004 | Zubok et al. |
| 2004/0176843 A1 | 9/2004 | Zubok et al. |
| 2004/0243240 A1 | 12/2004 | Beaurain et al. |
| 2005/0055029 A1 | 3/2005 | Marik et al. |
| 2005/0071013 A1 | 3/2005 | Zubok et al. |
| 2005/0085909 A1 | 4/2005 | Eisermann |
| 2005/0143820 A1* | 6/2005 | Zucherman et al. ...... 623/17.11 |
| 2005/0143821 A1 | 6/2005 | Zdeblick et al. |
| 2005/0149193 A1* | 7/2005 | Zucherman et al. ...... 623/17.11 |
| 2005/0154462 A1 | 7/2005 | Zucherman et al. |
| 2005/0159819 A1* | 7/2005 | McCormack et al. .... 623/17.16 |
| 2005/0192586 A1 | 9/2005 | Zucherman et al. |
| 2005/0197703 A1 | 9/2005 | Diaz et al. |
| 2005/0197706 A1 | 9/2005 | Hovorka et al. |
| 2006/0030862 A1 | 2/2006 | De Villiers et al. |

FOREIGN PATENT DOCUMENTS

| | | |
|---|---|---|
| DE | 3023353 | 4/1981 |
| EP | 0042271 | 12/1981 |
| EP | 0179695 | 4/1986 |
| EP | 0566810 | 10/1993 |
| EP | 0599419 | 6/1994 |
| EP | 0699426 | 3/1996 |
| EP | 0747025 | 12/1996 |
| FR | 2710519 | 4/1995 |
| FR | 2718635 | 10/1995 |
| FR | 2730159 | 8/1996 |
| WO | WO-90/00037 | 1/1990 |
| WO | WO-91/13598 | 9/1991 |
| WO | WO-92/14423 | 9/1992 |
| WO | WO-93/10725 | 6/1993 |
| WO | WO-94/04100 | 3/1994 |
| WO | WO-94/26893 | 11/1994 |
| WO | WO-95/08306 | 3/1995 |
| WO | WO-95/31947 | 11/1995 |

* cited by examiner

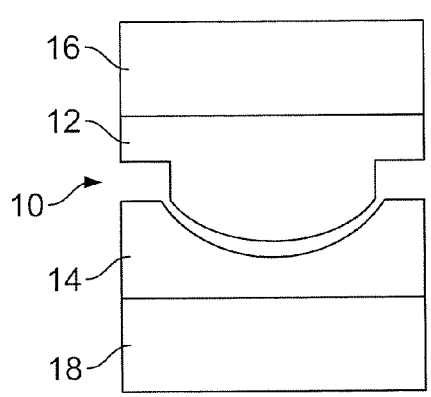
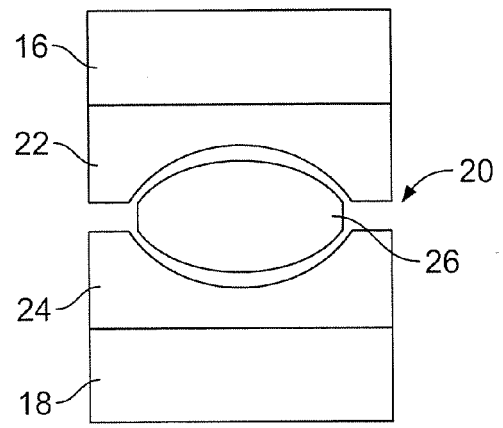
FIG. 1    FIG. 2
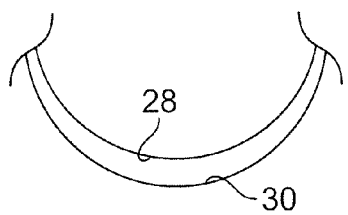
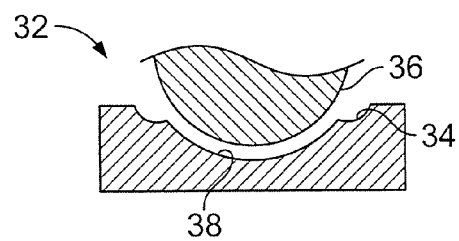
FIG. 3    FIG. 4
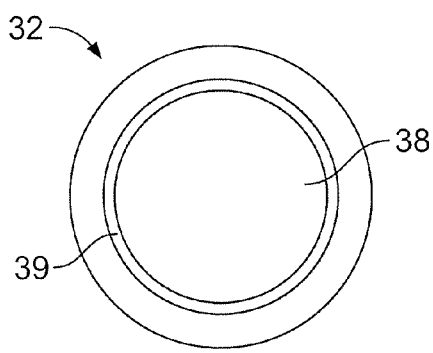
FIG. 5

INTERVERTEBRAL IMPLANTATION APPARATUS

CROSS-REFERENCE TO RELATED APPLICATIONS

This application claims the benefit of U.S. Provisional Application No. 60/830,153 filed on Jul. 11, 2006. The disclosure of the above application is incorporated herein by reference.

INTRODUCTION

Various spinal implants are known and/or are commercially available for use in replacing the natural intervertebral disc.

The present teachings provide an implantation apparatus that can include an intervertebral implant and associated instruments for facilitating implantation.

SUMMARY

The present teachings provide an implantation apparatus for preparing adjacent vertebral bodies to receive an intervertebral implant including a plurality of keels. The implantation apparatus includes an elongated handle portion, and a template portion carried at a distal end of the handle portion substantially perpendicularly to the handle portion. The template portion defines a plurality of open channels corresponding in position and shape to the plurality of keels. Each channel is positioned and shaped for preparing a vertebral opening to receive a corresponding keel.

In one aspect, the intervertebral implant can include first and second components defining first and second articulating surfaces, respectively. One of the implant components can define a lubrication groove circumscribing the corresponding articulating surface.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 1 is a simplified side view of a two-piece artificial disc prosthesis according to the present teachings;

FIG. 2 is a simplified side view of a three-piece artificial disc prosthesis according to the present teachings;

FIG. 3 is an enlarged, simplified view of an interface between articular surfaces of an artificial disc prosthesis according to the present teachings;

FIG. 4 is a simplified view of an artificial disc prosthesis including a recess to improve lubrication according to the present teachings;

FIG. 5 a simplified plan view of an articular surface of another artificial disc prosthesis according to the present teachings;

DESCRIPTION OF VARIOUS ASPECTS

Figure 6A:
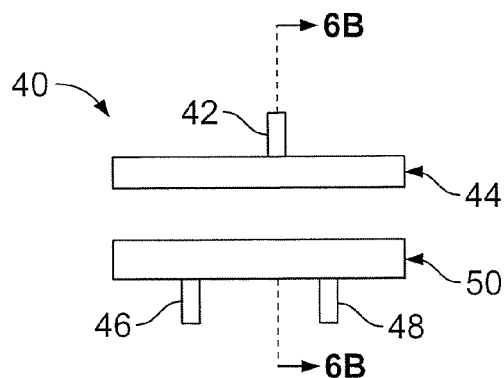
FIG. 6A is a simplified front view of another artificial disc prosthesis including at least one plate with spaced apart keels according to the present teachings.
Figure 6B:
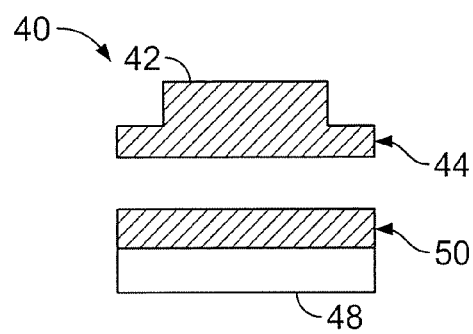
FIG. 6B is a cross-sectional view taken along the line 6B-6B.

The following description is merely exemplary in nature and is in no way intended to limit the invention, its application, or uses.

With reference to the simplified view of FIG. 1, an artificial disc prosthesis 10 may include first and second plates 12 and 14. The artificial disc prosthesis may be implanted between adjacent vertebral bodies 16 and 18 and referred to as an intervertebral implant. The plates 12 and 14 may be cooperatively configured to retain at least a range of the normal anatomical motion between the vertebral bodies 16 and 18 through direct contact and articulation.

Turning to the simplified side view of FIG. 2, an alternate artificial disc prosthesis 20 may be configured to include upper and lower plates 22 and 24 that cooperate with a core 26 positioned therebetween. The core 26 may independently articulate relative to the upper and lower plates 22, 24. As shown, the core 26 may include convex surfaces that cooperate with concave surfaces defined by the plates 22 and 24. Alternatively, the core 26 may include concave surfaces that cooperate with convex surfaces defined by the plates 22 and 24.

Turning to the simplified view of FIG. 3, an interface between cooperating first and second surfaces 28 and 30 of an artificial disc prosthesis is illustrated. The first and second articular surfaces 28 and 30 are smooth surfaces with specific tolerances to allow for increased and/or optimal fluid lubrication therebetween. Alternatively, the surfaces 28 and 30 may be dimpled or otherwise interrupted. The first and second surfaces 28 and 30 may be defined by first and second plates 12 and 14 as shown in FIG. 1, for example. Alternatively, the first and second surfaces 28 and 30 may be defined between a core 26 and one of an upper plate 22 or a lower plate 24 as shown in FIG. 2, for example. The tolerances between the two surfaces 28 and 30 may be within a range of approximately 10 to 250 microns. More particularly, the tolerances between the two surfaces 28 and 30 may be within a range of approximately 20 to 75 microns.

Turning to the simplified view of FIG. 4, an alternative artificial disc prosthesis 32 may include a recess 34 that may function as a fluid reservoir to provide additional lubrication to cooperating first and second articular surfaces 36 and 38. The first and second surfaces 36 and 38 may be defined by first and second plates 12 and 14 as shown in FIG. 1, for example. Alternatively, the first and second surfaces 36 and 38 may be defined between a core 26 and one of an upper plate 22 or a lower plate 24 as shown in FIG. 2, for example. The recess 34 may partially or complete circumferentially surround the articular surfaces 36 and 38.

Turning to the simplified view of FIG. 5, a plan view of an exemplary articular surface 38 of an exemplary artificial disc prosthesis 32 is illustrated. The articular surface 38 may include a recess 39 to provide additional lubrication. The recess 39 may define a closed-loop geometry. The closed-loop may be a circle, for example. The recess 39 may be defined in a convex surface or a concave articulating surface. The recess 39 may be carried by a plate of an artificial disc prosthesis or a core of an artificial disc prosthesis.

An alternative artificial disc prosthesis 40 may include one or more outwardly extending keels to provide fixation relative to an adjacent vertebral body. As shown in the simplified front view of FIG. 6, the artificial disc prosthesis 40 may include a single keel 42 on a first plate 44 and a pair of keels 46 and 48 on a second plate 50. The single keel 42 may be positioned on the anterior-posterior centerline of the corresponding plate 44 (as shown in FIG. 6) or disposed at a given distance from the centerline. The pair of keels 46 and 48 on the other plate 50 may be spaced equally from the centerline or otherwise spaced from the centerline. A greater separation between the pair of keels 46 and 48 may provide additional stability for the artificial disc prosthesis 40 and thereby facilitate multi-level procedures, because of the interdigitation of alternative keels. The prosthesis 40 may alternatively include two or more spaced apart keels extending from both plates. For example, the prosthesis 40 may include three keels extending from both plates. It will be understood that the prosthesis 40 may be a two piece prosthesis or a three piece prosthesis.

Figure 6C:
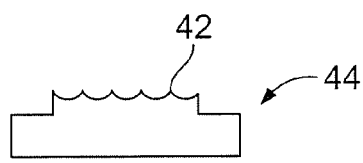
FIG. 6C is a simplified side view of a portion of another artificial disc prosthesis according to the present teachings.
Figure 6D:
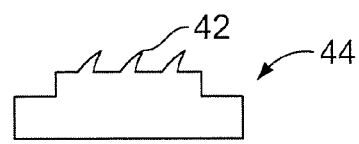
FIG. 6D is a simplified side view of a portion of another artificial disc prosthesis according to the present teachings.
Figure 6E:
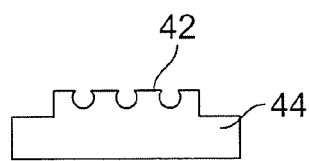
FIG. 6E is a simplified side view of a portion of another artificial disc prosthesis according to the present teachings.
Figure 6F:
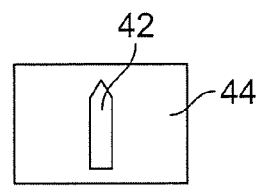
FIG. 6F is a simplified top view of a portion of another artificial disc prosthesis.
Figure 6G:
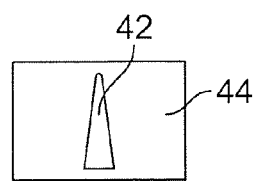
FIG. 6G is a simplified top view of a portion of another artificial disc prosthesis according to the present teachings.
Figure 6H:
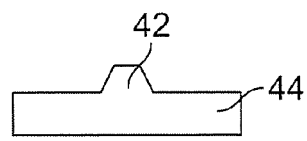
FIG. 6H is a simplified front view of a portion of another artificial disc prosthesis according to the present teachings.

The keels may vary in length in the anterior-posterior direction. The keels may have a leading edge and may be a constant height throughout the entire length. The tops of the keels may include structure for enhanced fixation with the adjacent vertebral bodies. Enhanced fixation may result from bone ingrowth in a direction toward the plate and/or in a direction perpendicular thereto and between the keel structures. Exemplary structures are shown in FIGS. 6C through 6E in relation to a representative keel 42. As shown in the simplified side view of FIG. 6C, the structure may include scallops/grooves. As shown in the simplified side view of FIG. 6D, the structure may include teeth or barbs. As shown in the simplified side view of FIG. 6E, the structure may include openings, which may be partially circular as shown in side view, or of any other geometry. As shown in the simplified top views of FIGS. 6F and 6G, the keels may taper in the anterior-posterior direction. As particularly shown in FIG. 6F, the taper may be limited to a forward/anterior portion of the keel. As particularly shown in FIG. 6G, the taper may extend substantially along the entire length of the keel. Alternatively, any portion of the keel may be tapered along its length in the anterior-posterior direction. As shown in the simplified front view of FIG. 6H, the keel may be tapered in an inferior-superior direction. Any combination of keel shape, size and orientation is contemplated according to the present teachings.

Figure 7:
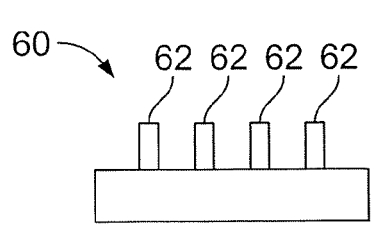
FIG. 7 is simplified side view of another artificial disc prosthesis include a plurality of pegs according to the present teachings.

Turning to the simplified side view of FIG. 7, an alternative artificial disc prosthesis may include a plate 60 with one or more keels or pegs 62 for fixation relative to an adjacent vertebral body. The pegs 62 may allow for enhanced bone ingrowth between adjacent pegs 62 after implantation so as to provide resistance to migration of the artificial disc prosthesis. The pegs 62 may include tapered or non-tapered sides. The top surfaces of the pegs 62 may be angled and/or tapered to facilitate insertion and/or resist migration. The pegs 62 may be positioned along an anterior-posterior centerline. Alternatively, the pegs 62 may be placed anywhere on the plate. The pegs 62 may be used as the sole structure for fixation to the adjacent vertebral bodies or may be used in combination with one or more keels or other fixation structures.

Figure 8:
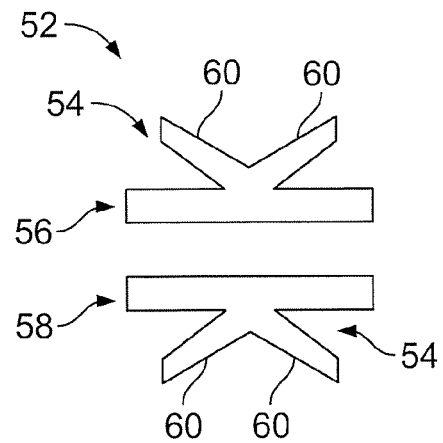
FIG. 8 is a simplified front view of another artificial disc prosthesis including keels that diverge in a medial-lateral direction according to the present teachings.

Turning to the simplified side view of FIG. 8, another artificial disc prosthesis 52 is illustrated. The artificial disc prosthesis 50 may include a keels 54 on a first plate 56 and a second plate 58. One or both of the keels 54 may include a pair of diverging arms 60. The arms 60 may linearly extend at an angle relative to the associated plate 56 and 58. Other geometries of the keels that have diverging arms may also be employed. It will be understood that the prosthesis 40 may be a two piece prosthesis or a three piece prosthesis.

Figure 9:
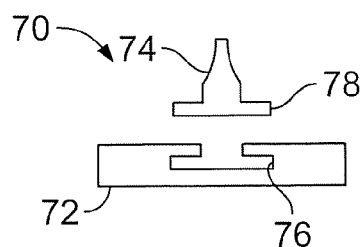
FIG. 9 is a simplified exploded view of a portion of another artificial disc prosthesis according to the present teachings.

Turning to the simplified front view of FIG. 9, a portion of another artificial disc prosthesis 70 is illustrated. The prosthesis 70 may be a modular structure including a plate 72 and a keel 74. The plate 72 may define a slot 76 for receiving a corresponding base 78 of the keel 74. The keel 74 may be press-fit within the slot or otherwise suitably secured within the slot 76.

Figure 10:
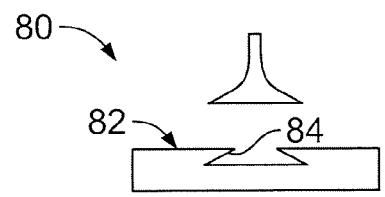
FIG. 10 is a simplified front view of a plate of another artificial disc prosthesis for receiving a modular keel according to the present teachings.

Turning to the simplified front view of FIG. 10, a plate 80 of yet another artificial disc prosthesis 82 for receiving a modular keel is illustrated. The plate 80 defines a dovetail slot 84 for receiving a corresponding structure of a keel. The keel may be press-fit within the slot or otherwise suitably secured within the slot 84.

Figure 11A:
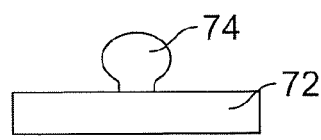
FIGS. 11A and 11B are simplified front and side views of another plate of an artificial disc prosthesis according to the present teachings.
Figure 11B:
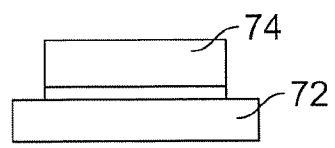
Figure 12A:
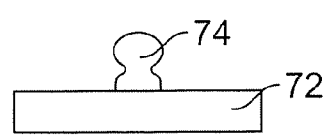
FIGS. 12A and 12B are simplified front and side views of another plate of an artificial disc prosthesis according to the present teachings.
Figure 12B:
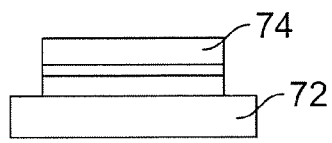

Turning to the simplified views of FIGS. 11A-11B and 12A-12B, alternate keel constructions 74 are illustrated. The keel constructions 74 of FIGS. 11A-11B and FIGS. 12A-12B incorporate one or more generally cylindrical portions. Apertures in the associated vertebral bodies may be more readily prepared for such geometries through the use of a conventional drill. FIGS. 11A-11B show a keel construction 74 with a single cylindrical portion. FIGS. 12A-12B show a keel construction 74 with two generally cylindrical portions.

Fixation to adjacent vertebral bodies may be further enhanced through surface treatment of the plates of the intervertebral implant. For example, the plates may be treated with a titanium plasma spray with HA coating. Additionally, the plates may be roughened in a known manner and treated with a peptide nano coating.

The plates and cores of the intervertebral implant may be constructed of any suitable material, including but not limited to metal, polyethylene, PEAK® and ceramic.

Figure 13:
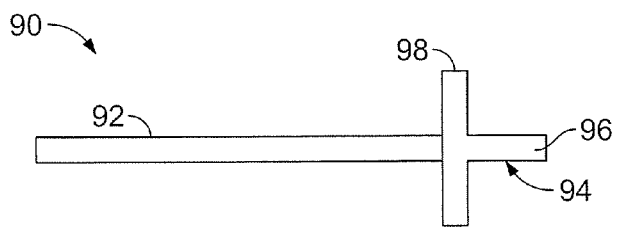
FIG. 13 is a side view of an instrument for preparing vertebral bodies according to the present teachings.
Figure 14:
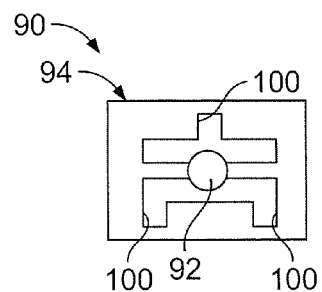
FIG. 14 is a front view of the instrument for preparing vertebral bodies of FIG. 13.

Turning to FIGS. 13 and 14, an instrument 90 for preparing adjacent vertebral bodies is illustrated. The instrument 90 is illustrated to include an elongated handle 92 and a forward portion 94 carried by the elongated handle 92. The forward portion 94 includes spacer portion 96 for insertion into the disc space between the adjacent vertebral bodies. The spacer portion 96 may maintain a proper distance between the adjacent vertebral bodies.

The forward portion 94 may additionally include a template portion 98 oriented in a plane substantially perpendicular to the spacer portion 96. The template portion 98 may function to both provide a stop for limiting insertion of the spacer portion 96 into the disc space and a template for cutting grooves in the adjacent vertebral bodies to receive keels, pegs or other fixation structure carried by the plates of the intervertebral implant. The template portion 98 may define a structure for forming channels or other openings corresponding in number, position, and shape, including size, to the number, position, and shape of keels carried by a specific intervertebral implant. In one exemplary use, the template portion 98 shown in FIG. 14 may be used to prepare adjacent vertebral bodies for receiving the simplified artificial disc prosthesis 40 shown in FIG. 6 to include a first plate having a single keel and a second plate having a pair of keels. In this regard, the template portion 98 defines slots or open channels 100 that correspond to the number, the location and shape of the keels of the prosthesis 40.

Figure 15:
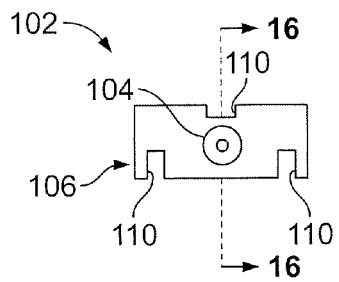
FIG. 15 is a cross-sectional view of another instrument for preparing vertebral bodies, the view taken through the line 15-15 of FIG. 16.
Figure 16:
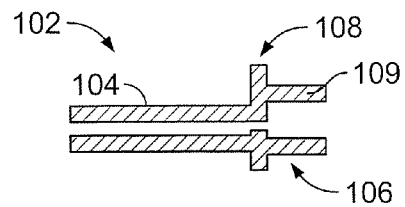
FIG. 16 is a front view of the instrument for preparing vertebral bodies of FIG. 15.

In use, the spacer portion 96 is inserted into the disc space and the template portion 98 is positioned adjacent to or substantially adjacent to the vertebral bodies. A cutting tool may be placed over the elongated handle 92 or other guiding structure. The cutting tool may be a chisel or other tool for forming grooves in the adjacent vertebral bodies. The grooves for the keels may be formed simultaneously or one at a time in the vertebral bodies Turning to FIGS. 15 and 16, an alternate instrument 102 for preparing adjacent vertebral bodies is illustrated. The instrument 102 is illustrated to include an elongated, cannulated handle 104 and a forward portion 106 carried by the elongated handle 104. The forward portion 106 includes spacer portion 109 for insertion into the disc space between the adjacent vertebral bodies. The spacer portion 109 may maintain a proper distance between the adjacent vertebral bodies.

The forward portion 106 may additionally include a template portion 108 oriented in a plane substantially perpendicular to the spacer portion 109. The template portion 108 may function to both provide a stop for limiting insertion of the spacer portion into the disc space and a template for cutting grooves in the adjacent vertebral bodies to receive keels, pegs or other fixation structure carried by the plates of the intervertebral implant. The template portion 108 may define a structure for forming channels corresponding in number, position, and shape to the number, position, and shape of keels carried by a specific implant. In one exemplary use, the template portion 108 shown in FIG. 14 may be used to prepare adjacent vertebral bodies for receiving the simplified artificial disc prosthesis 40 shown in FIG. 6 to include a first plate 44 having a single keel 42 and a second plate 50 having a pair of keels 46, 48. In this regard, the template portion 108 defines open channels 110 that correspond with the number, location and shape of the keels of the prosthesis 40.

Figure 17:
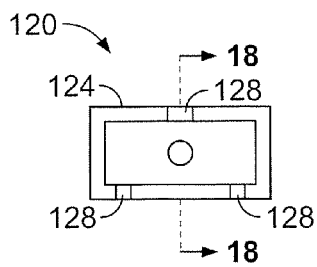
FIG. 17 is front view of another instrument for preparing vertebral bodies according to the present teachings.
Figure 18:
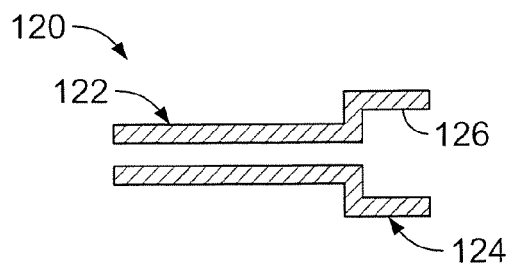
FIG. 18 is a cross-sectional view of the instrument for preparing vertebral bodies of FIG. 17 taken along the line 18-18 of FIG. 17.

Turning to FIGS. 17 and 18, another alternate instrument 120 for preparing adjacent vertebral bodies is illustrated. The instrument 120 is again illustrated to include an elongated, cannulated handle 122 and a forward portion 124 carried by the elongated handle 122. The instrument 120 is adapted to slidably receiving an elongated handle of a spacer or other guiding device. The forward portion 124 defines a box-like cavity 126 for receiving a spacer while positioned in the disc space. The forward portion 124 defines a plurality of cutters 128 for cutting channels into adjacent vertebral bodies. The instrument 120 may be tapped into the vertebral disc space to prepare the adjacent vertebral bodies for receipt of a keeled intervertebral implant. In one exemplary use, the instrument 120 may be used to prepare adjacent vertebral bodies for receiving the simplified artificial disc prosthesis 40 shown in FIG. 6 to include a first plate having a single keel 42 and a second plate having a pair of keels 46, 48. In this regard, the instrument 120 includes three cutters 128 that correspond with the location and shape of the keels of the prosthesis 40.

Figure 19:
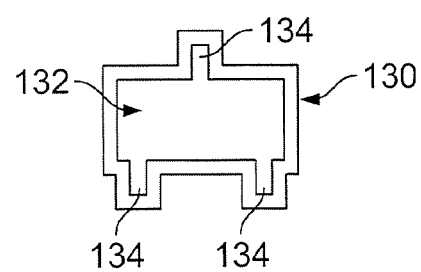
FIG. 19 is an end view of a guide tube and keel punch for preparing vertebral bodies to receive a keeled prosthesis according to the present teachings.

Turning to the end view of FIG. 19, illustrated are a guide tube 130 and cooperating keel punch 132. The guide tube 130 may partially extend into or be positioned adjacent to the vertebral disc space. The guide tube 130 slidably receives the keel punch 132. The keel punch 132 defines a plurality of cutters 134 for cutting channels into adjacent vertebral bodies. The punch 134 may be tapped into the vertebral disc space to prepare the adjacent vertebral bodies for receipt of a keeled prosthesis. In one exemplary use, the guide tube 130 and keel punch 132 may be used to prepare adjacent vertebral bodies for receiving the simplified artificial disc prosthesis 40 shown in FIG. 6 to include a first plate having a single keel 42 and a second plate having a pair of keels 46, 48. In this regard, the punch 132 includes three cutters 134 that correspond with the location and shape of the keels of the prosthesis 40.

During implantation of an artificial disc prosthesis, the natural disc may be removed and the disc space may be distracted. The disc space may be distracted with a series of spacers. The series of spacers may include a series of constant thickness, flat spacers. The flat spacers may be stacked to increase the disc space to a desired height. After a desired height has been obtained, a hollow distraction device may be placed into the disc space to maintain the desired height. The hollow device may define a generally rectangular cavity. The spacers may include a threaded aperture to facilitate insertion and/or removal. Similar distraction may be achieved through insertion of a constant thickness spacer between two opposing plates. Alternately, a series of flat, incrementally sized blocks may be sequentially introduced into the disc space to gradually increase the disc space.

Figure 20:
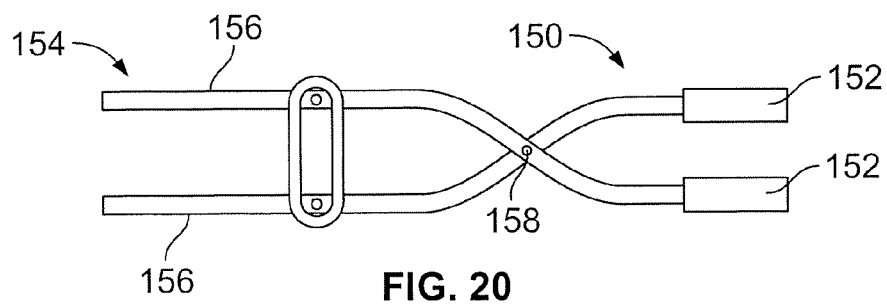
FIG. 20 is a side view of a distraction tool according to the present teachings.

Referring to FIG. 20, distraction of the disc space may alternatively be accomplished by mechanically driving the adjacent vertebral bodies apart using a distraction tool 150 having a pair of jaws 152. The jaws 152 may be inserted into the disc space and driven part to distract the intervertebral space. The distraction tool 150 can incorporate a handle 154 having two handle members 156 pivotally coupled about a pivot joint 158. The handle members 156 can be squeezed toward one another to facilitate distraction through a reverse scissor type action in which movement of the handles 156 toward one another functions to distract the jaws 152. Relative driven motion between the jaws 152 may be linear by making the jaws 152 parallel to one another. Alternatively, the jaws 152 can be driven apart with a threaded expandable mechanism through rotation of a shaft (not shown).

The foregoing discussion discloses and describes various features of intervertebral implants, methods for implanting intervertebral implants and instrumentation for implanting intervertebral implants. It will be appreciated that the various features described herein may be used alone or in any combination. Furthermore, it will be appreciated that an intervertebral implant incorporating one or more such features may be implanted with the methods and instrumentation described herein or alternatively with other suitable methods and instrumentation. One skilled in the art will readily recognize from such discussion, and from the accompanying drawings and claims, that various changes, modifications and variations can be made therein without departing from the spirit and scope of the present teachings as defined in the following claims.

What is claimed is:

1. An implantation apparatus comprising:
 an intervertebral implant including a plurality of keels extending outwardly from the implant, wherein the plurality of keels includes at least one keel modularly coupled to the implant, the implant including a first component having at least first and second keels, the first and second keels including a pair of diverging arms engageable with a first vertebra, and wherein the first and second keels are non-parallel; and
 an implantation tool comprising:
  a handle portion; and
  a template portion carried at a distal end of the handle portion substantially orthogonally to the handle portion; the template portion including a plurality of open channels, wherein the location and shape of each channel is determined by the location and shape of a corresponding keel.

2. The implantation apparatus of claim 1, wherein the plurality of channels includes at least first and second channels for at least partially overlying a first vertebral body.

3. The implantation apparatus of claim 1, further comprising a spacer portion forwardly extending from the template portion, the spacer portion extendable into the disc space between adjacent vertebral bodies.

4. The implantation apparatus of claim 3, wherein the template portion includes a stop surface substantially perpendicular to the spacer portion for limiting insertion of the spacer portion into the disc space.

5. The implantation apparatus of claim 1, further comprising a cutting tool couplable with the handle portion, the cutting tool including a cutting portion for forming grooves in the adjacent vertebral bodies through the plurality of channels corresponding to the plurality of keels.

6. The implantation apparatus of claim 1, further comprising a keel punch including a plurality of cutters for forming grooves in the adjacent vertebral bodies through the plurality of channels corresponding to the plurality of keels.

7. An implantation apparatus comprising:
 an intervertebral implant including a plurality of keels extending outwardly from the implant, wherein the plurality of keels includes at least one keel modularly coupled to the implant with a dovetail connection; and
 an implantation tool comprising:
  a handle portion; and
  a template portion carried at a distal end of the handle portion substantially orthogonally to the handle portion, the template portion including a plurality of open channels, wherein the location and shape of each channel is determined by the location and shape of a corresponding keel.

8. The apparatus of claim 7, wherein the plurality of keels includes first and second keels engageable with first and second adjacent vertebral bodies, and wherein the plurality of channels includes corresponding first and second channels configured for at least partially overlying the corresponding first and second vertebral bodies.

9. The apparatus of claim 7, wherein the plurality of keels includes first and second keels engageable with a first vertebral body, and wherein the plurality of channels includes corresponding first and second channels configured for at least partially overlying the corresponding first vertebral body.

10. The apparatus of claim 7, further comprising a spacer portion forwardly extending from the template portion, the spacer portion receivable into the disc space between adjacent vertebral bodies.

11. The apparatus of claim 1, wherein the first component includes a plate portion and the first and second keels linearly extend at an angle relative to the plate portion.

12. The implantation apparatus of claim 1, wherein the plurality of channels includes at least a first channel for at least partially overlying a first vertebral body and a second channel for at least partially overlying a second vertebral body.

13. The apparatus of claim 7, wherein the implant includes a lubrication reservoir recess.

* * * * *